(12) United States Patent
Takayama et al.

(10) Patent No.: US 6,566,113 B1
(45) Date of Patent: May 20, 2003

(54) POLYPEPTIDE HAVING CELLOBIOHYDROLASE ACTIVITY

(75) Inventors: Masanori Takayama, Kyotanabe (JP); Kahoko Umeda, Otsu (JP); Nobuto Koyama, Uji (JP); Kiyozo Asada, Koka-gun (JP); Ikunoshin Kato, Uji (JP)

(73) Assignee: Takara Shuzo Co., Ltd. (JP)

( * ) Notice: Subject to any disclaimer, the term of this patent is extended or adjusted under 35 U.S.C. 154(b) by 0 days.

(21) Appl. No.: 09/869,197

(22) PCT Filed: Dec. 14, 1999

(86) PCT No.: PCT/JP99/07009

§ 371 (c)(1),
(2), (4) Date: Jun. 25, 2001

(87) PCT Pub. No.: WO00/39288

PCT Pub. Date: Jun. 7, 2000

(30) Foreign Application Priority Data

Dec. 24, 1998 (JP) ............................................. 10-366237

(51) Int. Cl.[7] .......................... C12N 9/42; C12N 15/56; C12P 19/04

(52) U.S. Cl. .................... 435/209; 435/252.3; 435/101; 536/23.2

(58) Field of Search ................................. 435/209, 252, 435/3, 101; 536/23.2

(56) References Cited

U.S. PATENT DOCUMENTS 5,789,228 A    8/1998   Lam et al.

FOREIGN PATENT DOCUMENTS

WO            98/33895    *   8/1998

OTHER PUBLICATIONS

Gueguen, Y., et al. (1997) J. Biol. Chem. 272(50), 31258–31264.*

Kawarabayashi et al. (1998), "Complete Sequence and Gene Organization of the Genome of a Hyper–thermophilic Archaebacterium, *Pyrococcus horikoshii* OT3", *DNA Research*, 5:55–76.

* cited by examiner

Primary Examiner—Charles L. Patterson, Jr.
(74) Attorney, Agent, or Firm—Browdy and Neimark, PLLC

(57) ABSTRACT

Polypeptides having the amino acid sequence represented by SEQ ID NO:1 or derived therefrom by at least one of deletion, addition, insertion or substitution of one or more amino acids in the above sequence and showing a cellobiohydrolase activity.

8 Claims, 7 Drawing Sheets

SEQUENCE LISTING

<160> NUMBER OF SEQ ID NOS: 6

<210> SEQ ID NO 1
<211> LENGTH: 430
<212> TYPE: PRT
<213> ORGANISM: Pyrococcus horikoshii OT3

<400> SEQUENCE: 1

```
Glu Asn Thr Thr Tyr Gln Thr Pro Thr Gly Ile Tyr Tyr Glu Val Arg
1               5                   10                  15

Gly Asp Thr Ile Tyr Met Ile Asn Val Thr Ser Gly Glu Glu Thr Pro
            20                  25                  30

Ile His Leu Phe Gly Val Asn Trp Phe Gly Phe Glu Thr Pro Asn His
        35                  40                  45

Val Val His Gly Leu Trp Lys Arg Asn Trp Glu Asp Met Leu Leu Gln
    50                  55                  60

Ile Lys Ser Leu Gly Phe Asn Ala Ile Arg Leu Pro Phe Cys Thr Glu
65                  70                  75                  80

Ser Val Lys Pro Gly Thr Gln Pro Ile Gly Ile Asp Tyr Ser Lys Asn
                85                  90                  95

Pro Asp Leu Arg Gly Leu Asp Ser Leu Gln Ile Met Glu Lys Ile Ile
            100                 105                 110

Lys Lys Ala Gly Asp Leu Gly Ile Phe Val Leu Leu Asp Tyr His Arg
        115                 120                 125

Ile Gly Cys Thr His Ile Glu Pro Leu Trp Tyr Thr Glu Asp Phe Ser
    130                 135                 140

Glu Glu Asp Phe Ile Asn Thr Trp Ile Glu Val Ala Lys Arg Phe Gly
145                 150                 155                 160

Lys Tyr Trp Asn Val Ile Gly Ala Asp Leu Lys Asn Glu Pro His Ser
                165                 170                 175

Val Thr Ser Pro Pro Ala Ala Tyr Thr Asp Gly Thr Gly Ala Thr Trp
            180                 185                 190

Gly Met Gly Asn Pro Ala Thr Asp Trp Asn Leu Ala Ala Glu Arg Ile
        195                 200                 205

Gly Lys Ala Ile Leu Lys Val Ala Pro His Trp Leu Ile Phe Val Glu
    210                 215                 220

Gly Thr Gln Phe Thr Asn Pro Lys Thr Asp Ser Ser Tyr Lys Trp Gly
225                 230                 235                 240

Tyr Asn Ala Trp Trp Gly Gly Asn Leu Met Ala Val Lys Asp Tyr Pro
                245                 250                 255

Val Asn Leu Pro Arg Asn Lys Leu Val Tyr Ser Pro His Val Tyr Gly
            260                 265                 270

Pro Asp Val Tyr Asn Gln Pro Tyr Phe Gly Pro Ala Lys Gly Phe Pro
        275                 280                 285

Asp Asn Leu Pro Asp Ile Trp Tyr His His Phe Gly Tyr Val Lys Leu
    290                 295                 300

Glu Leu Gly Tyr Ser Val Val Ile Gly Glu Phe Gly Lys Tyr Gly
305                 310                 315                 320

His Gly Gly Asp Pro Arg Asp Val Ile Trp Gln Asn Lys Leu Val Asp
                325                 330                 335

Trp Met Ile Glu Asn Lys Phe Cys Asp Phe Phe Tyr Trp Ser Trp Asn
            340                 345                 350

Pro Asp Ser Gly Asp Thr Gly Gly Ile Leu Gln Asp Asp Trp Thr Thr
```

Ile Trp Glu Asp Lys Tyr Asn Asn Leu Lys Arg Leu Met Asp Ser Cys
370                 375                 380

Ser Lys Ser Ser Ser Thr Gln Ser Val Ile Arg Ser Thr Thr Pro
385                 390                 395                 400

Thr Lys Ser Asn Thr Ser Lys Lys Ile Cys Gly Pro Ala Ile Leu Ile
                405                 410                 415

Ile Leu Ala Val Phe Ser Leu Leu Leu Arg Arg Ala Pro Arg
            420                 425                 430

<210> SEQ ID NO 2
<211> LENGTH: 1293
<212> TYPE: DNA
<213> ORGANISM: Pyrococcus horikoshii OT3

<400> SEQUENCE: 2

```
gaaaatacaa catatcaaac accgactgga atttactacg aagtgagagg agatacgata    60
tacatgatta atgtcaccag tggagaggaa actcccattc atctctttgg tgtaaactgg   120
tttggctttg aaacacctaa tcatgtagtg cacggacttt ggaagagaaa ctgggaagac   180
atgcttcttc agatcaaaag cttaggcttc aatgcaataa gacttccttt ctgtactgag   240
tctgtaaaac caggaacaca accaattgga atagattaca gtaaaaatcc agatcttcgt   300
ggactagata gcctacagat tatggaaaag atcataaaga aggccggaga tcttggtatc   360
tttgtcttac tcgactatca taggatagga tgcactcaca tagaaccccct ctggtacacg   420
gaagacttct cagaggaaga ctttattaac acatggatag aggttgccaa aaggttcggt   480
aagtactgga acgtaatagg ggctgatcta aagaatgagc tcatagtgt tacctcaccc    540
ccagctgctt atacagatgg taccggggct acatggggta tgggaaaccc tgcaaccgat   600
tggaacttgg cggctgagag gataggaaaa gcgattctga aggttgcccc tcattggttg   660
atattcgtgg aggggacaca atttactaat ccgaagactg acagtagtta caaatggggc   720
tacaacgctt ggtggggagg aaatctaatg gccgtaaagg attatccagt taacttacct   780
aggaataagc tagtatacag ccctcacgta tatgggccag atgtctataa tcaaccgtac   840
tttggtcccg ctaagggttt tccggataat cttccagata tctggtatca ccactttgga   900
tacgtaaaat tagaactagg atattcagtt gtaataggag agtttggagg aaaatatggg   960
catggaggcg atccaaggga tgttatatgg caaaataagc tagttgattg gatgatagag  1020
aataaatttt gtgatttctt ttactggagc tggaatccag atagtggaga taccggaggg  1080
attctacagg atgattggac aacaatatgg gaagataagt ataataacct gaagagattg  1140
atggatagtt gttccaaaag ttcttcaagt actcaatccg ttattcggag taccacccct  1200
acaaagtcaa atacaagtaa gaagatttgt ggaccagcaa ttcttatcat cctagcagta  1260
ttctctcttc tcttaagaag ggctcccagg tag                               1293
```

<210> SEQ ID NO 3
<211> LENGTH: 25
<212> TYPE: DNA
<213> ORGANISM: Artificial Sequence
<220> FEATURE:
<223> OTHER INFORMATION: Designed oligonucleotide primer designated as
      1171FN to amplify a 1.6-kb DNA fragment containing the open
      reading frame PH1171

<400> SEQUENCE: 3
cggccatgga ggggaatact attct                                           25

<210> SEQ ID NO 4
<211> LENGTH: 25
<212> TYPE: DNA
<213> ORGANISM: Artificial Sequence
<220> FEATURE:
<223> OTHER INFORMATION: Designed oligonucleotide primer designated as
      1171RA to amplify a 1.6-kb DNA fragment containing the open
      reading frame PH1171

<400> SEQUENCE: 4
agaaattttc cataaaaggg gtcgc                                         25

<210> SEQ ID NO 5
<211> LENGTH: 458
<212> TYPE: PRT
<213> ORGANISM: Pyrococcus horikoshii OT3

<400> SEQUENCE: 5

```
Met Glu Gly Asn Thr Ile Leu Lys Ile Val Leu Ile Cys Thr Ile Leu
1               5                   10                  15

Ala Gly Leu Phe Gly Gln Val Val Pro Val Tyr Ala Glu Asn Thr Thr
            20                  25                  30

Tyr Gln Thr Pro Thr Gly Ile Tyr Tyr Glu Val Arg Gly Asp Thr Ile
        35                  40                  45

Tyr Met Ile Asn Val Thr Ser Gly Glu Glu Thr Pro Ile His Leu Phe
    50                  55                  60

Gly Val Asn Trp Phe Gly Phe Glu Thr Pro Asn His Val Val His Gly
65                  70                  75                  80

Leu Trp Lys Arg Asn Trp Glu Asp Met Leu Leu Gln Ile Lys Ser Leu
                85                  90                  95

Gly Phe Asn Ala Ile Arg Leu Pro Phe Cys Thr Glu Ser Val Lys Pro
            100                 105                 110

Gly Thr Gln Pro Ile Gly Ile Asp Tyr Ser Lys Asn Pro Asp Leu Arg
        115                 120                 125

Gly Leu Asp Ser Leu Gln Ile Met Glu Lys Ile Ile Lys Lys Ala Gly
    130                 135                 140

Asp Leu Gly Ile Phe Val Leu Leu Asp Tyr His Arg Ile Gly Cys Thr
145                 150                 155                 160

His Ile Glu Pro Leu Trp Tyr Thr Glu Asp Phe Ser Glu Glu Asp Phe
                165                 170                 175

Ile Asn Thr Trp Ile Glu Val Ala Lys Arg Phe Gly Lys Tyr Trp Asn
            180                 185                 190

Val Ile Gly Ala Asp Leu Lys Asn Glu Pro His Ser Val Thr Ser Pro
        195                 200                 205

Pro Ala Ala Tyr Thr Asp Gly Thr Gly Ala Thr Trp Gly Met Gly Asn
    210                 215                 220

Pro Ala Thr Asp Trp Asn Leu Ala Ala Glu Arg Ile Gly Lys Ala Ile
225                 230                 235                 240

Leu Lys Val Ala Pro His Trp Leu Ile Phe Val Glu Gly Thr Gln Phe
                245                 250                 255

Thr Asn Pro Lys Thr Asp Ser Ser Tyr Lys Trp Gly Tyr Asn Ala Trp
            260                 265                 270

Trp Gly Gly Asn Leu Met Ala Val Lys Asp Tyr Pro Val Asn Leu Pro
        275                 280                 285

Arg Asn Lys Leu Val Tyr Ser Pro His Val Tyr Gly Pro Asp Val Tyr
    290                 295                 300
```

```
Asn Gln Pro Tyr Phe Gly Pro Ala Lys Gly Phe Pro Asp Asn Leu Pro
305                 310                 315                 320

Asp Ile Trp Tyr His His Phe Gly Tyr Val Lys Leu Glu Leu Gly Tyr
                325                 330                 335

Ser Val Val Ile Gly Glu Phe Gly Lys Tyr Gly His Gly Gly Asp
            340                 345                 350

Pro Arg Asp Val Ile Trp Gln Asn Lys Leu Val Asp Trp Met Ile Glu
            355                 360                 365

Asn Lys Phe Cys Asp Phe Phe Tyr Trp Ser Trp Asn Pro Asp Ser Gly
    370                 375                 380

Asp Thr Gly Gly Ile Leu Gln Asp Asp Trp Thr Thr Ile Trp Glu Asp
385                 390                 395                 400

Lys Tyr Asn Asn Leu Lys Arg Leu Met Asp Ser Cys Ser Lys Ser Ser
                405                 410                 415

Ser Ser Thr Gln Ser Val Ile Arg Ser Thr Thr Pro Thr Lys Ser Asn
            420                 425                 430

Thr Ser Lys Lys Ile Cys Gly Pro Ala Ile Leu Ile Ile Leu Ala Val
            435                 440                 445

Phe Ser Leu Leu Leu Arg Arg Ala Pro Arg
    450                 455

<210> SEQ ID NO 6
<211> LENGTH: 1377
<212> TYPE: DNA
<213> ORGANISM: Pyrococcus horikoshii OT3

<400> SEQUENCE: 6
atggagggga atactattct taaaatcgta ctaatttgca ctattttagc aggcctattc      60
gggcaagtcg tgccagtata tgcagaaaat acaacatatc aaacaccgac tggaatttac    120
tacgaagtga gaggagatac gatatacatg attaatgtca ccagtggaga ggaaactccc    180
attcatctct tggtgtaaa ctggtttggc tttgaaacac taatcatgt agtgcacgga     240 ctttggaaga gaaactggga agacatgctt cttcagatca aaagcttagg cttcaatgca    300 ataagcttc ctttctgtac tgagtctgta aaaccaggaa cacaaccaat tggaatagat     360
tacagtaaaa atccagatct tcgtggacta gatagcctac agattatgga aaagatcata    420 agaaggccg agatcttgg tatctttgtc ttactcgact atcataggat aggatgcact     480
cacatagaac ccctctgta cacggaagac ttctcagagg aagactttat taacacatgg     540
atagaggttg ccaaaaggtt cggtaagtac tggaacgtaa tagggctga tctaaagaat     600 gagcctcata gtgttacctc accccagct gcttatacag atggtaccgg ggctacatgg     660
ggtatgggaa accctgcaac cgattggaac ttggcggctg agaggatagg aaaagcgatt    720
ctgaaggttg cccctcattg gttgatattc gtggagggga cacaatttac taatccgaag    780
actgacagta gttacaaatg gggctacaac gcttggtggg gaggaaatct aatggccgta    840
aaggattatc cagttaactt acctaggaat aagctagtat acagccctca cgtatatggg    900
ccagatgtct ataatcaacc gtactttggt cccgctaagg gttttccgga taatcttcca    960
gatatctggt atcaccactt tggatacgta aaattagaac taggatattc agttgtaata   1020
ggagagtttg gaggaaaata tggcatggga ggcgatccaa gggatgttat atggcaaaat   1080
aagctagttg attggatgat agaaataaa ttttgtgatt tcttttactg gagctggaat   1140
ccagatagtg gagataccgg agggattcta caggatgatt ggacaacaat atgggaagat   1200
```

```
aagtataata acctgaagag attgatggat agttgttcca aaagttcttc aagtactcaa    1260
tccgttattc ggagtaccac ccctacaaag tcaaatacaa gtaagaagat ttgtggacca    1320
gcaattctta tcatcctagc agtattctct cttctcttaa gaagggctcc caggtag       1377
```

POLYPEPTIDE HAVING CELLOBIOHYDROLASE ACTIVITY

REFERENCE TO RELATED APPLICATIONS

The present application is the national stage under 35 U.S.C. §371 of international application PCT/JP99/07009, filed Dec. 14, 1999 which designated the United States, and which application was not published in the English language.

TECHNICAL FIELD

The present invention relates to a polypeptide, more specifically, a polypeptide having an activity of degrading cellulose, which is useful for profitable utilization of biomass. The present invention also relates to a gene that is useful for producing said polypeptide by genetic engineering.

BACKGROUND ART

Cellulose is represented by $(C_6H_{10}O_5)_n$. Materials containing cellulose as the main component are exemplified by woods such as pines, cedars, beeches and poplars; stalks and basts such as hemps, paper bushes, rice straws, bagasse and chaff; seed downs such as cotton; old papers such as newspapers, magazines and corrugated cardboard waste papers; other fibrous wastes; pulps, cellulose powder and the like. Recently, old papers from offices are increasing.

A cellulose molecule has a structure in which D-glucopyranose is connected though β-1,4 bonds and has no side chain. Thus, cellulose is composed of glucose, which can be used as a raw material in alcohol fermentation. If cellulose could be degraded into glucose, it would be possible to produce alcohol, which is useful as a fuel and the like, from old papers or fibrous wastes.

Hydrolysis of cellulose into glucose by an acid method or an enzymatic method has been conducted as a method for degrading (saccharifying) cellulose. In the acid method, cellulose is contacted with hydrochloric acid or sulfuric acid to violently degrade a mass of fibers. Since it is difficult to appropriately determine the hydrolysis conditions, the resulting glucose may further react in the presence of a strong acid. Thus, the acid method has a problem of difficulty in recovering glucose with a high yield and the like. Therefore, the acid method is not utilized practically now. To the contrary, the enzymatic method using a cellulose hydrolase has high reaction selectivity and is advantageous in view of environmental protection. Thus, the enzymatic method has become the mainstream of hydrolysis methods. Various methods have been reported [Wood, B. E., et al., Biothechnology Progress, 13:223–237 (1997); U.S. Pat. No. 5,508,183; Zhao Xin, et al., Enzyme Microbial Technology, 15:62–65 (1993), etc.].

Cellulose hydrolases are exemplified by endoglucanase (EC 3.2.1.4), β-D-glucosidase (EC 3.2.1.21), exo-1,4-β-D-glucosidase (EC 3.2.1.74) and cellobiohydrolase (EC 3.2.1.91). The recommended name of endoglucanase is cellulase, and the systematic name is 1,4-(1,3,1,4)-β-D-glucan 3(4)-glucanohydrolase.

A mixture consisting of endoglucanase, β-D-glucosidase, exo-1,4-β-D-glucosidase, cellobiohydrolase and the like is usually used for hydrolyzing cellulose. Such enzymes cooperatively act on cellulose to degrade it into glucose. Several theories are known for the mode of action. Murao et al. has proposed the following model. First, cleavages are introduced into the non-crystalline regions of cellulose by the action of endoglucanase. Cellobiohydrolase acts on the gaps while destroying the crystal. oligosaccharides are produced by the action of endoglucanase and cellobiohydrolase. The oligosaccharides are degraded by the action of β-D-glucosidase to generate glucose [Sawao Murao et al, "Cellulase", pp. 102–104, Kodansha (May 10, 1987)].

In most cases, cellulose does not exist as a single cellulose chain. A structure in which many cellulose chains are assembled through hydrogen bond is formed. In this structure, there are crystalline regions in which a number of cellulose chains are densely clustered and non-crystalline regions in which cellulose chains are sparsely placed. The rate-determining step in a hydrolysis reaction by an enzymatic method is a step of separating and dispersing many cellulose chains in the crystalline regions. Accordingly, conducting a reaction for enzymatic degradation at a high temperature has the following advantages: (1) the reaction proceeds efficiently since cellulose crystals are readily destroyed; (2) risk of contamination with miscellaneous bacteria is little; and (3) cooling prior to an enzymatic reaction is not required in a industrial process which requires heating.

β-D-glucosidase from *Pyrococcus furiosus*, β-D-glucosidase from *Thermococcus* sp., endoglucanase and β-D-glucosidase from *Thermotoga maritima*, endoglucanase and β-D-glucosidase from *Thermotoga neapolitana* and the like are known as cellulose hydrolases from extreme thermophiles [Bauer, et al., Current Opinion in Biotechnology, 9:141–145 (1998)]. Cloning of β-D-glucosidase gene from an extreme thermophile is described, for example, in U.S. Pat. No. 5,744,345. Cloning of endoglucanase gene from an extreme thermophile is described, for example, in WO 97/44361.

Cellobiohydrolase has been isolated from a thermophilic bacterium, Thermotoga sp. FjSS-B.1 [Ruttersmith, et al., Biochemical Journal, 277:887–890 (1991)]. Since the inhibition constant (Ki) of this enzyme for cellobiose is low (0.2 mM), the enzyme is liable to product inhibition. The specific activity using 4-methylumbelliferyl-β-D-cellobioside as a substrate is 3.6 U/mg. Furthermore, since the bacterium should be cultured at a high temperature under anaerobic conditions, it is difficult to industrially produce the enzyme in large quantities. Additionally, since a gene encoding the enzyme has not been cloned, the enzyme cannot be produced by genetic engineering.

OBJECTS OF THE INVENTION

The main object of the present invention is to provide cellobiohydrolase having a high inhibition constant for cellobiose and heat resistance, as well as means to produce said cellobiohydrolase at low cost.

SUMMARY OF THE INVENTION

The nucleotide sequence of the entire pyrococcus horikoshii OT3 genomic DNA has been determined [Kawarabayasi, et al., DNA Research, 5:55–76 (1998); Kawarabayasi, et al., DNA Research, 5:147–155 (1998)]. A list of proteins having homologies in amino acid sequences with gene products deduced from the respective open reading frames has been published (http://www.bio.nite.go.jp/ot3db_index.html). Existence of open reading frames encoding polypeptides such as α-amylase, α-mannosidase, β-D-galactosidase, β-D-glucosidase, β-D-mannosidase and endoglucanase in *Pyrococcus horikoshii* OT3 genome has been predicted based on the comparison of homologies with nucleic acids encoding known cellulose hydrolases in this list. However, existence of an open reading frame having a homology with a nucleic acid encoding a known cellobiohydrolase has not been predicted.

As a result of intensive studies, the present inventors have found that there exists an open reading frame (PH1171) in *Pyrococcus horikoshii* OT3 genome which encodes a polypeptide having a cellobiohydrolase activity. Unexpectedly, it proved that the polypeptide having the amino acid sequence encoded by the open reading frame has a cellobiohydrolase activity although it has a homology with various endoglucanases including endoglucanase from an archaebacterium AEPIIIa. Furthermore, the present inventors have established a method for producing the polypeptide by genetic engineering. Thus, the present invention has been completed.

The present invention provides the following.

(1) a polypeptide having the amino acid sequence of SEQ ID NO:1 or an amino acid sequence in which one or more amino acid residue is deleted, added, inserted and/or substituted in the amino acid sequence of SEQ ID NO:1 and having a cellobiohydrolase activity;

(2) the polypeptide according to (1) above, which has a thermostable cellobiohydrolase activity;

(3) a nucleic acid encoding the polypeptide according to (1) or (2) above;

(4) the nucleic acid according to (3) above, which has the nucleotide sequence of SEQ ID NO:2;

(5) a nucleic acid encoding a polypeptide having a cellobiohydrolase activity which is capable of hybridizing to the nucleic acid according to (3) above under stringent conditions;

(6) the nucleic acid according to (5) above, which encodes a polypeptide having a thermostable cellobiohydrolase activity;

(7) a recombinant DNA containing the nucleic acid according to any one of (3) to (6) above;

(8) a transformant transformed with the recombinant DNA according to (7) above;

(9) a method for producing the polypeptide according to (1) above, the method comprising culturing the transformant according to (8) above and collecting a polypeptide having a cellobiohydrolase activity from the culture;

(10) a method for degrading a polymer of D-glucopyranose bonded through β-1,4 bonds, the method comprising allowing the polypeptide according to (1) above to act on a polymer of D-glucopyranose bonded through β-1,4 bonds to release cellobiose;

(11) a polypeptide having a cellobiohydrolase activity and having an inhibition constant Ki of 10 mM or more for cellobiose; and

(12) the polypeptide according to (11) above, which retains 20% or more of the cellobiohydrolase activity after treatment at 95° C. for 5 hours.

DETAILED DESCRIPTION OF THE INVENTION

Figure 1:
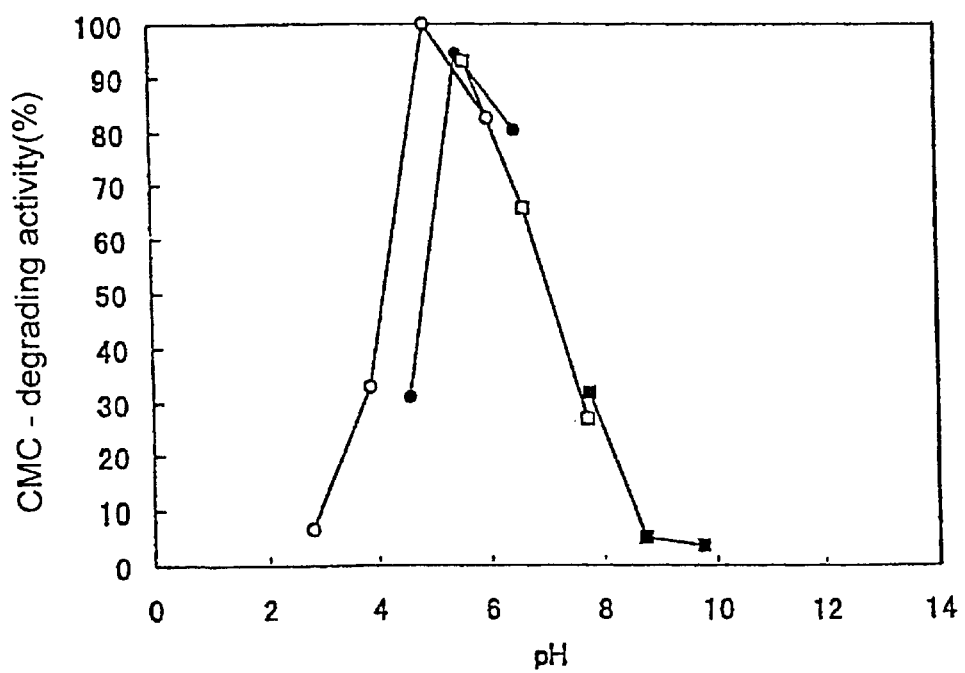
FIG. 1: a figure which illustrates the relationship between the CMC-degrading activity of the polypeptide of the present invention and the reaction pH.

1. The Polypeptide of the Present Invention

The polypeptide of the present invention is characterized by having the amino acid sequence of SEQ ID NO:1 or an amino acid sequence in which one or more amino acid residue is deleted, added, inserted and/or substituted in the amino acid sequence of SEQ ID NO:1 and having a cellobiohydrolase activity.

As used herein, a cellobiohydrolase activity means an activity that hydrolyzes a glucoside bond in a polysaccharide or an oligosaccharide consisting of D-glucose bonded through β-1,4 bonds to release cellobiose, a disaccharide in which D-glucose is bonded through a β-1,4 bond, but does not hydrolyze the glucoside bond in cellobiose. A method for measuring the cellobiohydrolase activity is exemplified by a known method in which an enzymatic reaction is carried out using phosphoric acid-swollen cellulose as a substrate and the existence of cellobiose in the reaction is confirmed by thin-layer silica gel chromatography.

The polypeptide of the preset invention has a cellobiohydrolase activity. The polypeptide may have other glycosidase activities such as an endoglucanase activity and a β-D-glucosidase activity.

In one embodiment, the polypeptide of the present invention is characterized by having a thermostable cellobiohydrolase activity.

As used herein, "heat resistance" means that a polypeptide has an enzymatic activity which is not irreversibly denatured (inactivated) when it is incubated under high temperature conditions in an industrial process for producing alcohol from biomass for a time required to degrade cellulose. As used herein, irreversible denaturation means permanent and complete loss of an enzymatic activity. Hereinafter, a cellobiohydrolase activity with heat resistance is referred to as a thermostable cellobiohydrolase activity. Although it is not intended to limit the present invention, the polypeptide having the amino acid sequence of SEQ ID NO:1 retains 80% or more of the cellobiohydrolase activity after treatment at 75° C. for 20 minutes, at 95° C. for 10 minutes, or at 95° C. for 5 hours. Furthermore, the polypeptide exhibits a cellobiohydrolase activity under high temperature conditions such as 90° C. or higher, or 100° C. or higher. The polypeptide of the present invention which has a thermostable cellobiohydrolase activity retains preferably 20% or more, more preferably 40% or more, most preferably 80% or more of the cellobiohydrolase activity after treatment at 95° C. for 5 hours.

The polypeptide having the amino acid sequence of SEQ ID NO:1 as an example of the polypeptide of the present invention has an activity of generating cellobiose from phosphoric acid-swollen cellulose or cellooligosaccharide, for example. The optimal pH for the thermostable cellobiohydrolase activity of the polypeptide is 5 to 6.5. The polypeptide exhibits a thermostable cellobiohydrolase activity at 65° C. to 113° C. The optimal temperature is about 110° C. The polypeptide has high heat resistance. It retains about 90% of the activity after heating in the presence of a substrate at pH 6 at 95° C. for 5 hours. About 80% of the activity remains after heating for additional 24 hours. The activity is not decreased when the polypeptide is heated in the absence of a substrate at 95° C. for 10 minutes at pH 5 to 7. When the cellobiohydrolase activity of the purified polypeptide is measured using 4-methylumbelliferyl-β-D-cellobioside as a substrate in a reaction at 98° C. at pH 6.0 for 20 minutes, the specific activity is 17.0 U/mg.

The polypeptide can act on carboxymethylcellulose (CMC) or cellooligosaccharide. The cellobiohydrolase activity of the polypeptide can also be measured using the amount of reducing end of sugar as an index, which reducing end is generated using CMC or cellooligosaccharide as a substrate. The polypeptide also acts on a chromophoric substrate such as p-nitrophenyl-β-D-cellobioside or a fluorescent substrate such as 4-methylumbelliferyl-β-D-cellobioside. Thus, the cellobiohydrolase activity of the polypeptide can be conveniently measured by measuring the amount of a chromophoric or fluorescent substance generated by the reaction.

The polypeptide exhibits the maximal thermostable cellobiohydrolase activity in the presence of 0.5 to 1.0 M NaCl. In the absence of NaCl, the polypeptide exhibits about 80% of the activity that exhibited in the presence of 0.5 M NaCl. In the presence of 2.5 M NaCl, the polypeptide exhibits about 60% of the activity that exhibited in the presence of 0.5 M NaCl. Thus, the effect of the NaCl concentration on the thermostable cellobiohydrolase activity is little.

In one embodiment, inhibition of the cellobiohydrolase activity of the polypeptide of the present invention by a reaction product such as cellobiose or glucose is little. The inhibition constant (Ki) of the polypeptide for cellobiose is preferably 10 mM or more, more preferably 30 mM or more, most preferably 100 mM or more. For example, the inhibition constant (Ki) of the polypeptide of the present invention having the amino acid sequence of SEQ ID NO:1 for cellobiose is 212 mM. No polypeptide having such a high inhibition constant for cellobiose was known prior to the present invention. Almost no inhibition of the activity by glucose is observed. Furthermore, the activity is inhibited by about 90% by 0.5 mM $Fe^{3+}$, $Cu^{2+}$ or $Zn^{2+}$, or by about 50% by 1 mM $Co^{2+}$, $Ca^{2+}$, $Mg^{2+}$ or ethylenediaminetetraacetic acid as compared with the activity in the absence of such reagent. Almost no inhibition of the activity by 10 mM dithiothreitol is observed.

The polypeptide of the present invention includes a polypeptide having an amino acid sequence in which one or more amino acid residue is deleted, added, inserted and/or substituted in the amino acid sequence of SEQ ID NO:1 as long as it exhibits a cellobiohydrolase activity.

A mutation such as deletion, insertion, addition or substitution of an amino acid in an amino acid sequence may be generated in a naturally occurring protein. Such mutation may be generated due to a polymorphism or a mutation of the DNA encoding the protein, or due to a modification of the protein in vivo or during purification after synthesis. However, it is known that such a mutated protein may exhibit physiological and biological activities substantially equivalent to those of a protein without a mutation if such a mutation is present in a portion that is not important for the retention of the activity or the structure of the protein.

This is applicable to a protein in which such a mutation is artificially introduced into an amino acid sequence of a protein. In this case, it is possible to generate more various mutations. For example, it is known that a polypeptide in which a cysteine residue in the amino acid sequence of human interleukin-2 (IL-2) is substituted with a serine retains the interleukin-2 activity (Science, 224:1431 (1984)).

Furthermore, it is known that certain proteins have peptide regions that are not indispensable to their activities. Such peptide regions are exemplified by a signal peptide in a protein to be secreted extracellularly or a prosequence found in a precursor of a protease. Most of such regions are removed after translation or upon conversion into an active protein. Such a protein has a primary structure different from that of a protein without the region to be removed, but finally exhibits an equivalent function. The amino acid sequence of SEQ ID NO:1 is a sequence in which a signal region of 28 amino acid residues at the N-terminus is removed from the amino acid sequence of SEQ ID NO:5. A nucleic acid having a nucleotide sequence of SEQ ID NO:6 encodes a polypeptide having the amino acid sequence of SEQ ID NO:5. When *Escherichia coli* harboring a vector containing this nucleic acid is cultured, the signal peptide region is removed from the expressed polypeptide, and the polypeptide having the amino acid sequence of SEQ ID NO:1 is produced.

When a protein is produced by genetic engineering, a peptide chain that is irrelevant to the activity of the protein of interest may be added at the amino terminus or the carboxyl terminus of the protein. For example, a fusion protein, in which a portion of an amino terminus region of a protein that is expressed at a high level in the host to be used is added at the amino terminus, may be prepared in order to increase the expression level of the protein of interest. Alternatively, a peptide having an affinity with a specific substance may be added at the amino terminus or the carboxyl terminus of the protein of interest in order to facilitate the purification of the expressed protein. The added peptide may remain added if it does not have a harmful influence on the activity of the protein of interest. If necessary, it may be engineered such that it can be removed from the protein of interest by appropriate treatment, for example, by limited digestion with a protease.

Thus, a polypeptide having an amino acid sequence in which one or more amino acid residue is deleted, inserted, added and/or substituted in the amino acid sequence disclosed herein (SEQ ID NO:1) is encompassed by the present invention as long as it has a cellobiohydrolase activity. Preferably, such a polypeptide has a thermostable cellobiohydrolase activity and a high inhibition constant for cellobiose.

The polypeptide of the present invention can be produced, for example, by (1) purification from a culture of a microorganism producing the polypeptide of the present invention, or (2) purification from a culture of a transformant containing a nucleic acid encoding the polypeptide of the present invention.

(1) Purification from Culture of Microorganism Producing the Polypeptide of the Present Invention The microorganism producing the polypeptide of the present invention is exemplified by *Pyrococcus horikoshii* OT3 (JCM9974) which can be purchased from Riken (the Institute of Physical and Chemical Research).

The microorganism is cultured under conditions suitable for the growth of the microorganism. Preferably, culture conditions which increase the expression level of the polypeptide of interest are used. The polypeptide of interest produced in the cells or the culture can be purified according to a method conventionally used for purifying a protein.

A method conventionally used for culturing a hyperthermophile can be utilized for the cultivation of the above-mentioned bacterial strain. Nutrients which can be utilized by the bacterial strain are added to the culture medium. For example, starch can be utilized as a carbon source, and Tryptone, peptone and yeast extract can be utilized as a nitrogen source. A metal salt such as a magnesium salt, a sodium salt or an iron salt may be added to a culture medium as a trace element. In addition, it may be advantageous to use artificial seawater for the preparation of a culture medium, for example. A clear culture medium which does not contain solid sulfur is desirable. By using such a culture medium, the growth of cells can be readily monitored by measuring the turbidity of the culture.

The culture may be a standing culture or a spinner culture. For example, a dialysis culture method as described in Applied and Environmental Microbiology, 55:2086–2088 (1992) may be used. In general, the culture temperature is preferably about 95° C. Usually, a significant amount of a polypeptide is accumulated in the culture after culturing for about 16 hours. It is preferable to determine the culture conditions depending on the cell or the composition of the culture medium to be used such that the productivity of the polypeptide becomes maximal.

A cell-free extract is first prepared in order to obtain a polypeptide. The cell-free extract can be prepared, for example, by collecting cells from a culture by centrifugation, filtration or the like and then disrupting the cells. A cell disruption method highly effective for extracting the enzyme of interest may be selected from sonication, disruption using beads, treatment with a lytic enzyme, treatment with a surfactant and the like. If the polypeptide is secreted into the culture, the polypeptide is concentrated by ammonium sulfate salting out, ultrafiltration or the like. The concentrated polypeptide is used as a cell-free extract. A method conventionally used for purifying a protein can be used to isolate the polypeptide from the thus obtained cell-free extract. For example, ammonium sulfate salting out, ion exchange chromatography, hydrophobic chromatography, gel filtration chromatography and the like can be used in combination.

(2) Purification from Culture of Transformant Transformed with Recombinant DNA Containing Nucleic Acid Encoding the Polypeptide of the Present Invention An exemplary nucleotide sequence of a nucleic acid encoding the polypeptide of the present invention is shown in SEQ ID NO:2. The amino acid sequence of the polypeptide of the preset invention deduced from the nucleotide sequence of SEQ ID NO:2 is shown in SEQ ID NO:1. Thus, an exemplary amino acid sequence of a polypeptide obtained according to the present invention is shown in SEQ ID NO:1.

The host to be transformed is not limited to specific one and exemplified by *Escherichia coli, Bacillus subtilis,* yeast and filamentous fungi.

For example, the polypeptide of the present invention can be obtained using *Escherichia coli* BL21 (DE3) harboring pECEL211, a plasmid in which the DNA of SEQ ID NO:6 is linked at downstream of T7 promoter. The amino acid sequence of the polypeptide of the preset invention deduced from the nucleotide sequence of SEQ ID NO:6 is shown in SEQ ID NO:5. *Escherichia coli* JM109 transformed with pECEL211 is designated and indicated as *Escherichia coli* JM109/pECEL211, and deposited on Dec. 11, 1998 at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM P-17075 and transmitted to international depositary authority under Budapest Treaty on Nov. 15, 1999 under accession number FERM BP-6939.

The polypeptide can be expressed in cultured cells by culturing *Escherichia coli* BL21 (DE3) harboring pECEL211 under conventional culture conditions, for example, in LB medium (10 g/l Tryptone, 5 g/l yeast extract, 5 g/l NaCl, pH 7.2) containing 100 μg/ml of ampicillin at 37° C. until logarithmic growth phase, adding isopropyl-β-D-thiogalactopyranoside at a final concentration of 0.1 mM thereto and further culturing at 15° C.

A supernatant prepared by collecting cells by centrifugation after cultivation, disrupted the cells by sonication and collecting a supernatant by centrifugation can be used as a cell-free extract. This cell-free extract can be used for an enzymatic reaction. The polypeptide of the present invention can be purified from the cell-free extract by using known methods such as ion exchange chromatography, gel filtration, hydrophobic chromatography and ammonium sulfate precipitation. Naturally, a partially purified product can also be used for an enzymatic reaction. Since the polypeptide of the present invention expressed from *Escherichia coli* BL21 (DE3) harboring pECE211 is highly thermostable, the cultured cells and/or the cell-free extract may be heated, for example, at 95° C. for 10 minutes for purification.

Alternatively, the polypeptide of the present invention can be obtained using *Bacillus subtilis* DB104 harboring pNCEL101, a plasmid in which the DNA of SEQ ID NO:2 is linked at downstream of the subtilisin promoter, for example. Specifically, the polypeptide of the present invention can be accumulated in a culture by culturing *Bacillus subtilis* DB104 harboring pNCEL101 under conventional culture conditions, for example, in LB medium containing 10 μg/ml of kanamycin at 37° C. overnight. The polypeptide of the present invention in the culture can be purified according to known methods as described above for the production using *Escherichia coli* as a host.

As described above, when the polypeptide of the present invention is expressed at normal temperature (e.g., 37° C.) using a nucleic acid encoding the polypeptide, the resulting expression product retains the activity, the heat resistance and the like. That is, the polypeptide of the present invention can assume its inherent higher-order structure even if it is expressed at a temperature quite different from the growth temperature of the original producer cell.

2. The Nucleic Acid of the Present Invention

The nucleic acid of the present invention is a nucleic acid that encodes the polypeptide of the present invention as described above. Specifically, it is exemplified by (1) a nucleic acid encoding a polypeptide having the amino acid sequence of SEQ ID NO:1 or an amino acid sequence in which one or more amino acid residue is deleted, added, inserted and/or substituted in the amino acid sequence of SEQ ID NO:1 and having a cellobiohydrolase activity; (2) a nucleic acid having the nucleotide sequence of SEQ ID NO:2; and (3) a nucleic acid encoding a polypeptide having a cellobiohydrolase activity which is capable of hybridizing to the nucleic acid of (1) or (2) above under stringent conditions.

As used herein, a nucleic acid means a single-stranded or double-stranded DNA or RNA.

If the nucleic acid of (2) above is an RNA, it is represented by a nucleotide sequence in which T is replaced by U in the nucleotide sequence of SEQ ID NO:2.

For example, the nucleic acid of the present invention can be obtained as follows.

The nucleic acid of (2) above having the nucleotide sequence of SEQ ID NO:2 can be isolated from *Pyrococcus horikoshii* OT3 (JCM9974, Riken) as described above for the polypeptide of the present invention.

Furthermore, a nucleic acid encoding a polypeptide having a cellobiohydrolase activity similar to that of the polypeptide of the present invention can be obtained on the basis of the nucleotide sequence of the nucleic acid encoding the polypeptide provided by the present invention. Specifically, a DNA encoding a polypeptide having a cellobiohydrolase activity can be screened by using the nucleic acid encoding the polypeptide of the present invention or a portion of the nucleotide sequence as a probe for hybridization or a primer for a gene amplification method such as a PCR. The nucleic acids of (1) and (3) above can be obtained according to such a method.

A nucleic acid fragment containing only a portion of the nucleic acid of interest may be obtained according to the above-mentioned method. In this case, the entire nucleic acid of interest can be obtained as follows. The nucleotide sequence of the obtained nucleic acid fragment is determined to confirm that the fragment is a portion of the nucleic acid of interest. Hybridization is carried out using the nucleic acid fragment or a portion thereof as a probe. Alternatively, a PCR is carried out using a primer synthesized on the basis of the nucleotide sequence of the nucleic acid fragment.

"Hybridize under stringent conditions" refers to being capable of hybridizing, for example, under the following conditions. A membrane onto which a nucleic acid is immobilized is incubated with a probe in 6×SSC (1×SSC: 0.15 M NaCl, 0.015 M sodium citrate, pH 7.0) containing 0.5% SDS, 0.1% bovine serum albumin (BSA), 0.1% polyvinylpyrrolidone, 0.1% Ficoll 400 and 0.01% denatured salmon sperm nucleic acid at 50° C. for 12 to 20 hours. After incubation, the membrane is washed in 2×SSC containing 0.5% SDS at 37° C. while changing the SSC concentration down to 0.1× and the temperature up to 50° C. until the signal from the immobilized nucleic acid can be distinguished from background, and the probe is then detected. The activity of the protein encoded by the thus obtained novel nucleic acid is determined as described above, thereby confirming whether or not the nucleic acid is the nucleic acid of interest.

Furthermore, the nucleic acid is incorporated into an appropriate expression vector or the like to construct a recombinant DNA containing the nucleic acid of the present invention. A transformant containing the recombinant DNA is then produced. The transformant can be used to industrially produce the polypeptide.

As described above, a nucleotide sequence which is not identical with the nucleotide sequence disclosed herein is encompassed by the present invention as long as it encodes a polypeptide having a cellobiohydrolase activity.

It is known that one to six codon (a combination of three bases), which defines an amino acid in a gene, is assigned for each amino acid. Thus, many nucleic acids can encode one specific amino acid sequence depending on the amino acid sequence. Nucleic acids are not stable in the nature. Generation of a mutation in a nucleotide sequence is not unusual. A mutation generated in a nucleic acid may not alter the encoded amino acid sequence (called as a silent mutation). In this case, it can be said that a different nucleic acid encoding the same amino acid sequence is generated. Thus, it cannot be denied that various nucleic acids encoding the same amino acid sequence can be generated in the course of passage of an organism containing an isolated nucleic acid encoding one specific amino acid sequence. Furthermore, it is not difficult to artificially produce various nucleic acids encoding the same amino acid sequence using various means for genetic engineering.

For example, if a codon used in an original nucleic acid encoding a protein of interest is one whose codon usage is low in the host to be used for producing the protein by genetic engineering, the expression level of the protein may be low. In this case, the codon is artificially converted into one frequently used in the host without altering the encoded amino acid sequence aiming at elevating the expression level of the protein of interest (e.g., JP-B 7-102146). As described above, various nucleic acids encoding one specific amino acid sequence can be artificially prepared, of course. They may also be generated in the nature.

3. The method for degrading polymer of D-glucopyranose bonded through β-1,4 bonds using the polypeptide of the present invention The polypeptide of the present invention can be used to release cellobiose from a polymer of D-glucopyranose bonded through β-1,4 bonds. The degree of polymerization of glucose in the polymer of D-glucopyranose bonded through β-1,4 bonds is not specifically limited in the present invention. The polymers include cellotriose and cellulose. The polypeptide of the present invention represented by SEQ ID NO:1 is highly thermostable. Partially due to a synergistic effect with the structural change of the substrate by heating, it can more efficiently degrade cellulose.

Specifically, cellobiose can be released by reacting, for example, the polypeptide having the amino acid sequence of SEQ ID NO:1 with a substrate in 50 mM MES-NaOH buffer (pH 6.0) at 98° C. Naturally, the reaction conditions may vary depending on the type of the substrate (cellulose, cellotetraose, etc.). The polypeptide of the present invention may be added to a substrate suspension in a free form. However, the polypeptide is readily recovered after reaction if it is reacted with a substrate being immobilized onto an appropriate carrier.

Furthermore, it is possible to degrade cellulose into D-glucose with high efficiency by using thermostable endoglucanase, exo-1,4-β-D-glucosidase and β-D-glucosidase together with the polypeptide of the present invention.

EXAMPLES

The following examples further illustrate the present invention in detail but are not to be construed to limit the scope thereof.

Among the procedures described herein, basic procedures including preparation of plasmid DNAs and restriction enzyme digestion were carried out as described in T. Maniatis, et al. (eds.), Molecular Cloning: A Laboratory Manual 2nd ed. (1989) Cold Spring Harbor Laboratory. Unless otherwise stated, *Escherichia coli* JM109 or HB101 were used as a host for the construction of plasmids using *Escherichia coli* and were cultured aerobically at 37° C. using LB medium (1% Tryptone, 0.5% yeast extract, 0.5% NaCl, pH 7.0) containing 100 μg/ml of ampicillin or LB plate prepared by adding agar at concentration of 1.5% to LB medium and solidifying the resulting mixture.

EXAMPLE 1

Construction of Recombinant DNA Containing Open Reading Frame PH1171 in *Pyrococcus horikoshii* OT3 Genome (1) Preparation of DNA Containing Open Reading Frame PH1171

An oligonucleotide 1171FN having the nucleotide sequence of SEQ ID NO:3 and an oligonucleotide 1171RA having the nucleotide sequence of SEQ ID NO:4 were synthesized on the basis of the nucleotide sequence of *Pyrococcus horikoshii* OT3 genome in order to obtain an about 1.6-kb amplified DNA fragment containing the open reading frame PH1171 by a PCR using *Pyrococcus horikoshii* OT3 genomic DNA as a template.

*Pyrococcus horikoshii* OT3 JCM9974 (purchased from Riken) was cultured in a medium as described in JCM catalog (Riken) at 95° C. for 16 hours. A genomic DNA was purified from the cultured cells.

A PCR was carried out using the oligonucleotides 1171FN and 1171RA as a primer pair and the above-mentioned genomic DNA as a template in order to obtain a DNA containing the open reading frame PH1171. The PCR was carried out according to the protocol attached to TaKaRa Ex Taq (Takara Shuzo) as follows: 25 cycles of 94° C. for 0.5 minute, 50° C. for 2 minutes and 94° C. for 1.5 minutes. The PCR product was subjected to agarose gel electrophoresis. An amplified DNA fragment of about 1.6 kb was extracted and purified. Analysis of the nucleotide sequence of the thus obtained DNA revealed that the DNA contained the open reading frame PH1171.

(2) Construction of Recombinant DNA pECEL101

The about 1.6-kb amplified DNA fragment obtained in (1) above was digested with restriction enzymes StuI and AvaI (both from Takara Shuzo), blunt-ended with T4 DNA polymerase (Takara Shuzo) and subjected to agarose gel electrophoresis. A DNA fragment of about 1.5 kb was then extracted and purified. On the other hand, pET21a (Novagen) was digested with a restriction enzyme BamHI (Takara Shuzo), dephosphorylated with alkaline phosphatase (Takara Shuzo) and blunt-ended with T4 DNA polymerase. The two blunt-ended DNA fragments were ligated using DNA ligase (Takara Shuzo). The ligation mixture was used to transform *Escherichia coli* JM109. Several transformants were selected, and plasmid DNAs contained in the respective transformants were purified. Restriction enzyme maps were prepared for the plasmid DNAs to select a plasmid DNA in which the open reading frame PH1171 was inserted in the same direction as that of T7 promoter in the vector. The selected plasmid DNA was designated as pECEL101.

(3) Construction of Recombinant DNA pECEL211

A recombinant DNA consisting of the about 1.6-kb amplified DNA fragment obtained in (1) above and pET21d (Novagen) was prepared as follows.

The about 1.6-kb amplified DNA fragment obtained in (1) above was digested with AvaI, blunt-ended with T4 DNA polymerase and digested with a restriction enzyme NcoI (Takara Shuzo) such that the first codon of PH1171 was operatively placed downstream from T7 promoter in pET21d. On the other hand, pET21d was digested with BamHI, blunt-ended with T4 DNA polymerase, digested with NcoI and dephosphorylated with alkaline phosphatase.

The two DNA fragments treated as described above were ligated using DNA ligase. The ligation mixture was used to transform *Escherichia coli* JM109. Several transformants were selected and cultured. Plasmid DNAs contained in the respective transformants were purified. Restriction enzyme maps were prepared for the plasmid DNAs to select a plasmid DNA into which PH1171 was inserted. The selected plasmid DNA was designated as pECEL211. *Escherichia coli* JM109 harboring pECEL211 is designated as *Escherichia coli* JM109/pECEL211, and deposited at the National Institute of Bioscience and Human-Technology, Agency of Industrial Science and Technology under accession number FERM BP-6939.

EXAMPLE 2

Production of the Polypeptide of the Present Invention (1) Expression of Polypeptide pECEL211 prepared in Example 1 (3) or pET21d as a vector control was used to transform *Escherichia coli* BL21 (DE3) (Novagen). Each of the resulting transformants was separately inoculated into 5 ml of LB medium containing 100 μg/ml of ampicillin, and cultured aerobically at 37° C. overnight. The culture was inoculated into 5 ml of the same fresh medium at a concentration of 1%, and cultured aerobically at 37° C. When the turbidity reached $OD_{600}$ =0.4 to 0.7, isopropyl-β-D-thiogalactopyranoside (IPTG, Takara Shuzo) was added at a final concentration of 1 mM. The cells were further cultured at 15° C. overnight. After cultivation, the cells were collected by centrifugation, suspended in 0.5 ml of 100 mM sodium citrate buffer (pH 5.0) and disrupted by sonication. Supernatants recovered after centrifugation were used as cell-free extracts.

When cellulose is degraded using a cellulose hydrolase such as endoglucanase or cellobiohydrolase, reducing ends of glucose residues are newly generated. Then, increase in the amount of reducing end in a unit reaction time was measured according to the Park and Johnson method using carboxymethylcellulose (CMC) as a substrate in order to confirm whether or not a polypeptide having an activity of hydrolyzing cellulose which newly generates reducing ends of glucose residues existed in the *Escherichia coli* extract.

A CMC solution was prepared by dissolving CMC (Sigma) in 100 mM sodium citrate buffer (pH 5.0) at a concentration of 1%. 50 μl of the CMC solution and 50 μl of a dilution of the cell-free extract with 100 mM sodium citrate buffer (pH 5.0) were mixed together, and the mixture was overlaid with mineral oil. After incubation at 98° C. for 60 minutes, the mixture was centrifuged to recover an aqueous layer. 10 μl of the reaction mixture, 90 μl of water, 100 μl of a carbonate cyanide solution and 100 μl of 0.05% potassium ferricyanide aqueous solution were mixed together and reacted for 15 minutes in boiling water. The carbonate cyanide solution was prepared by dissolving 5.3 g of sodium carbonate and 0.65 g of potassium cyanide in 1 liter of water. The reaction mixture was mixed with 500 μl of an iron alum solution. The iron alum solution was prepared by dissolving 1.5 g of iron alum and 1 g of sodium lauryl sulfate (SDS) in 1 liter of 0.15 N sulfuric acid. The resulting mixture was allowed to stand at room temperature for 15 minutes. Absorbance at 690 nm was then measured. The amount of reducing end was determined as the amount of corresponding glucose based on a calibration curve prepared using glucose at a known concentration.

One unit (U) of a CMC-degrading activity is defined as an activity that increases reducing power corresponding to 1 μmol of glucose in one minute in the above-mentioned reaction system.

The CMC-degrading activities of the respective cell-free extracts determined as described above are shown in Table 1. Table 1 is a table that shows CMC-degrading activities at 98° C. detected in the cell-free extracts prepared as described above.

TABLE 1

| Plasmid | CMC-degrading activity (mU/ml) |
| --- | --- |
| pECEL211 | 64 |
| pET21d | 0 |

As shown in Table 1, a CMC-degrading activity was clearly detected in the cell-free extract from *Escherichia coli* transformed with pECEL211, whereas no CMC-degrading activity was detected in the cell-free extract from *Escherichia coli* transformed with pET21d. Thus, it was demonstrated that the polypeptide expressed from the open reading frame PH1171 in *Pyrococcus horikoshii* OT3 genome had an activity of hydrolyzing cellulose which newly generates reducing ends of glucose residues.

(2) Identification of Activity of Hydrolyzing Cellulose of Expressed Polypeptide Before examining, an expressed polypeptide solution was prepared as follows.

*Escherichia coli* BL21 (DE3) harboring pECEL211 was inoculated into 10 ml of LB medium containing 50 μg/ml of ampicillin and cultured at 37° C. overnight. The culture was inoculated into 1 liter of the same medium and cultured at 37° C. for 2.5 hours. The culture vessel was cooled on ice. IPTG at a final concentration of 0.1 mM was added thereto. The cells were cultured at 20° C. overnight. The cells were collected by centrifugation, suspended in 50 ml of 20 mM sodium phosphate buffer (pH 7.0) and sonicated. A supernatant obtained by centrifugation was treated at 95° C. for 10 minutes and then centrifuged to obtain a supernatant. The thus obtained centrifuged supernatant was used as an expressed polypeptide solution in the subsequent experiments.

The activity of hydrolyzing cellulose of the expressed polypeptide was identified as follows. Specifically, the expressed polypeptide solution was allowed to act on various substrates. Products were then identified on thin-layer chromatography.

First, phosphoric acid-swollen cellulose was used as a substrate. Phosphoric acid-swollen cellulose was prepared as follows.

2 g of Avicel SF (Asahi Kasei) was slowly added to 50 ml of ice-cold 85% phosphoric acid. The mixture was stirred on ice while sonicating at intervals to dissolve Avicel SF. The solution was poured into 1.5 liter of ice water. Cellulose gel was recovered by centrifugation. The cellulose gel was washed six times in water to remove phosphoric acid and suspended in 40 ml of 0.1 M sodium citrate buffer (pH 5.0) and used as phosphoric acid-swollen cellulose in the subsequent experiments.

75 μl of the expressed polypeptide solution was added to 75 μl of the phosphoric acid-swollen cellulose. The mixture was reacted at 98° C. for 8 hours. 60 μl of acetonitrile was added to the equal volume of the reaction mixture and mixed. A supernatant obtained by centrifugation was evaporated under reduced pressure to dryness. The residue was dissolved in 10 μl of water. 2 μl of the solution was subjected to silica gel thin-layer chromatography. Two rounds of development were carried out using silica gel 60F254 (Merck) as a thin-layer plate and ethanol:butanol:water= 5:5:1 as a solvent for development. Orcinol-sulfuric acid reagent was sprayed onto the thin-layer plate after development and the plate was heated using a hot plate to observe the spots. The orcinol-sulfuric acid reagent was prepared by dissolving 400 mg of orcinol (Sigma) in 22.8 ml of sulfuric acid and adding water thereto to a total volume of 200 ml.

As a result, generation of cellobiose was demonstrated.

Second, various oligosaccharides were used as substrates.

Oligosaccharide solutions were prepared by dissolving cellobiose (Sigma), cellotriose, cellotetraose or cellopentaose (the latter three from Seikagaku Corporation) in 0.1 M MES-NaOH buffer (pH 6.0) at a concentration of 1% (w/v). 25 μl each of the oligosaccharide solutions was added to 25 μl of a 10-, 50- or 250-fold dilution of the expressed polypeptide solution with the MES buffer. The mixtures were reacted at 98° C. for 20 minutes. As controls, mixtures to which the MES buffer was added in place of the diluted expressed polypeptide solution or the oligosaccharide solution were reacted at the same time. 1 μl of a supernatant obtained by centrifugation after reaction was subjected to silica gel thin-layer chromatography as described above for the case where the phosphoric acid-swollen cellulose was used as a substrate. Two rounds of development were carried out when cellobiose, cellotriose or cellotetraose was used as a substrate. Three rounds of development were carried out when cellopentaose was used.

Spots for cellobiose, cellotriose, cellotetraose and cellopentaose as substrates were detected for reactions without the addition of the expressed polypeptide solution. No spot was detected when a substrate was not added to the reaction. When a reactions was carried out with the addition of the expressed polypeptide solution and one of the substrates, substances which resulted in spots with larger Rf values than that for the intact substrate were generated from each of the oligosaccharides except cellobiose. The amounts of the substances were increased depending on the amount of the expressed polypeptide solution added.

Reactions were carried out as described above using oligosaccharides as substrates except that the dilution rate of the expressed polypeptide solution was 10 and the reaction time was 2 hours. Supernatants obtained by centrifuging the reaction mixtures were analyzed on silica gel thin-layer chromatography as described above.

As a result, the substrates other than cellobiose were consumed almost completely. Cellotriose and cellotetraose generated cellobiose. Cellopentaose generated cellotriose and cellobiose. The principal degradation product was cellobiose for each of the respective oligosaccharides as substrates.

These results demonstrate that the polypeptide expressed from the open reading frame PH1171 in *Pyrococcus horikoshii* OT3 genome has a cellobiohydrolase activity.

EXAMPLE 3

Physical and Chemical Properties of Cellobiohydrolase Activity of the Polypeptide of the Present Invention The polypeptide solution of the present invention prepared in Example 2-(2) was used in this Example. Cellobiohydrolase activities were determined as the following activities: 1) a CMC-degrading activity determined by measuring the amount of cellobiose, which was generated using CMC as a substrate, as the amount of reducing sugar according to the Park and Johnson method; 2) a p-nitrophenyl-β-D-cellobioside (pNPC)-degrading activity determined by measuring the amount of cellobiose, which was generated using pNPC as a substrate, as the amount of p-nitrophenol; or 3) a 4-methylumbelliferyl-β-D-cellobioside (4-MUC)-degrading activity determined by measuring the amount of cellobiose, which was generated using 4-MUC as a substrate, as the amount of 4-methylumbelliferone (4-MU).

(1) Dependency Upon Reaction pH

The following buffers were prepared. 0.2 M sodium citrate buffers at pH 2.8, 3.8, 4.9 or 6.0, 0.2 M MES-NaOH buffers at pH 4.6, 5.5 or 6.5, 0.2 M Tris-HCl buffers at pH 5.6, 6.6 or 7.7 and 0.2 M glycine-NaOH buffers at pH 7.7, 8.7 or 9.8. pH was measured at 80° C.

50 μl of a 50-fold dilution of the polypeptide solution of the present invention with water, 25 μl of a 2% CMC aqueous solution and 25 μl of one of the above-mentioned buffers were mixed together. The mixture was reacted at 98° C. for 20 minutes. The amount of reducing sugar contained in a supernatant obtained by centrifuging the reaction mixture was measured according to the Park and Johnson method, and the CMC-degrading activity was calculated.

The results are shown in FIG. 1. FIG. 1 illustrates the relationship between the reaction pH and the CMC-degrading activity. The horizontal axis represents the pH and the vertical axis represents the CMC-degrading activity (relative value, %). Open circles (○), closed circles (●), open squares (□) and closed squares (■) represent the results for sodium citrate buffers, MES-NaOH buffers, Tris-HCl buffers and glycine-NaOH buffers, respectively.

The polypeptide of the present invention exhibited the maximal activity at pH 4.9 to 6.5.

(2) Dependency upon Reaction Temperature

50 μl of 1% CMC solution in 0.1 M MES-NaOH buffer (pH 6.0) was added to 50 μl of a dilution of the polypeptide solution of the present invention with 0.1 M MES-NaOH buffer (pH 6.0). The mixture was reacted at 37, 65, 98, 108 or 113° C. for 20 minutes. The amount of generated reducing sugar was measured according to the Park and Johnson method to determine the CMC-degrading activity.

Figure 2:
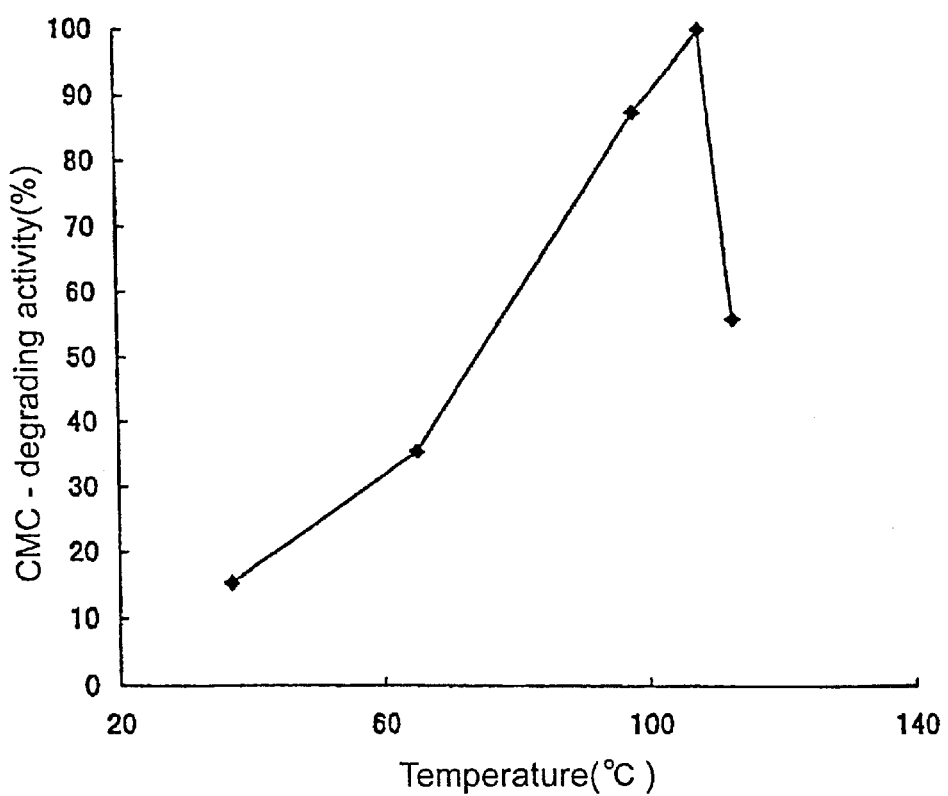
FIG. 2: a figure which illustrates the relationship between the CMC-degrading activity of the polypeptide of the present invention and the reaction temperature.

The results are shown in FIG. 2. FIG. 2 illustrates the relationship between the reaction temperature and the CMC-degrading activity of the polypeptide of the present invention. The horizontal axis represents the temperature (° C.) and the vertical axis represents the CMC-degrading activity (relative value, %).

The polypeptide of the present invention exhibited the maximal CMC-degrading activity at 108° C., about 80% of the maximal activity at 90° C. and about 60% of the maximal activity at 80° C.

(3) Effect of Salt Concentration

The polypeptide solution of the present invention was diluted 50-fold with water or 1, 2, 3, 4 or 5 M NaCl. 50 μμl of 1% CMC solution in 0.1 M MES-NaOH buffer (pH 6.0) was added to 50 μl of one of the dilution of the polypeptide solution of the present invention. The mixture was reacted at 98° C. for 20 minutes. The amount of the generated reducing sugar was measured according to the Park and Johnson method to determine the CMC-degrading activity.

Figure 3:
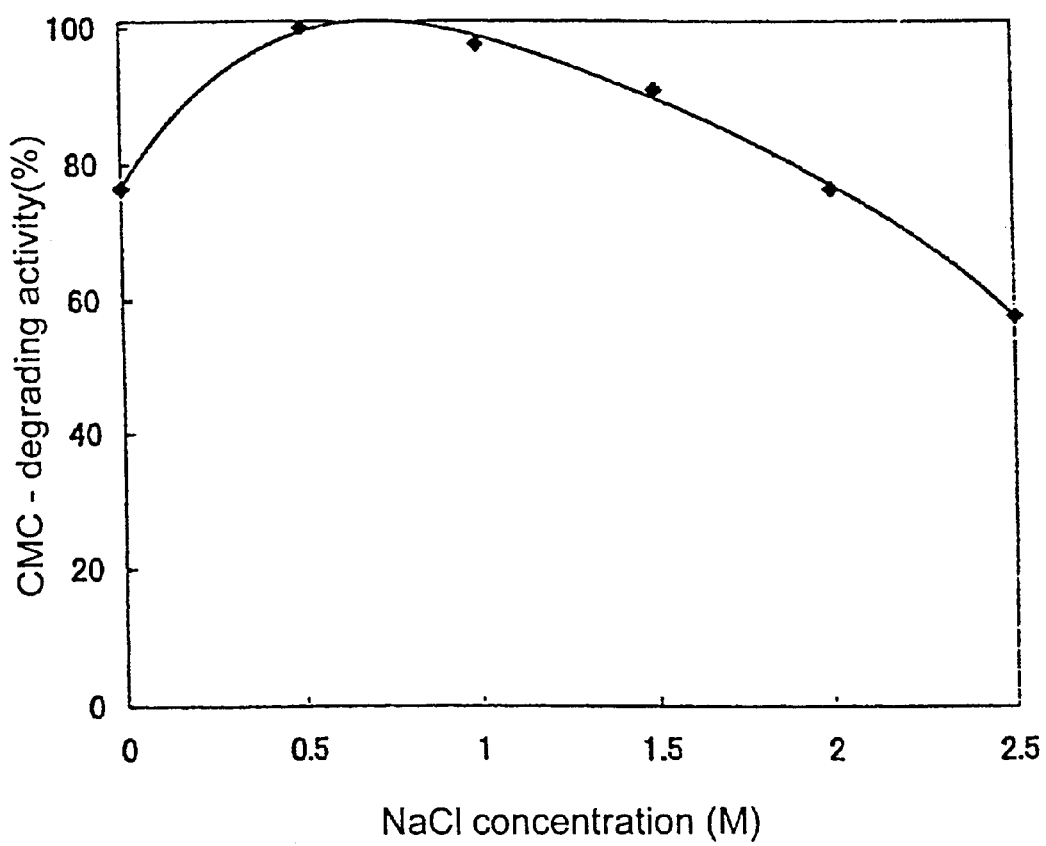
FIG. 3: a figure which illustrates the effect of the concentration of NaCl in the reaction mixture on the CMC-degrading activity of the polypeptide of the present invention.

The results are shown in FIG. 3. FIG. 3 illustrates the relationship between the NaCl concentration and the CMC-degrading activity of the polypeptide of the present invention. The horizontal axis represents the NaCl concentration (M) and the vertical axis represents the CMC-degrading activity (relative value, %).

The polypeptide of the present invention exhibited the maximal CMC-degrading activity in the presence of 0.5 to 0.6 M NaCl.

(4) pH Stability

25 μl of the polypeptide solution of the present invention and 25 μl of one of the buffers prepared in Example 3-(1) were mixed together. The mixture was heated at 95° C. for 10 minutes. 50 μl of 1% CMC solution in 0.1 M MES-NaOH buffer (pH 6.0) was added to 50 μl of a 50-fold dilution of the heated mixture with water. The mixture was reacted at 98° C. for 20 minutes. The amount of reducing sugar contained in a supernatant obtained by centrifuging the reaction mixture was measured according to the Park and Johnson method, and the CMC-degrading activity was calculated.

Figure 4:
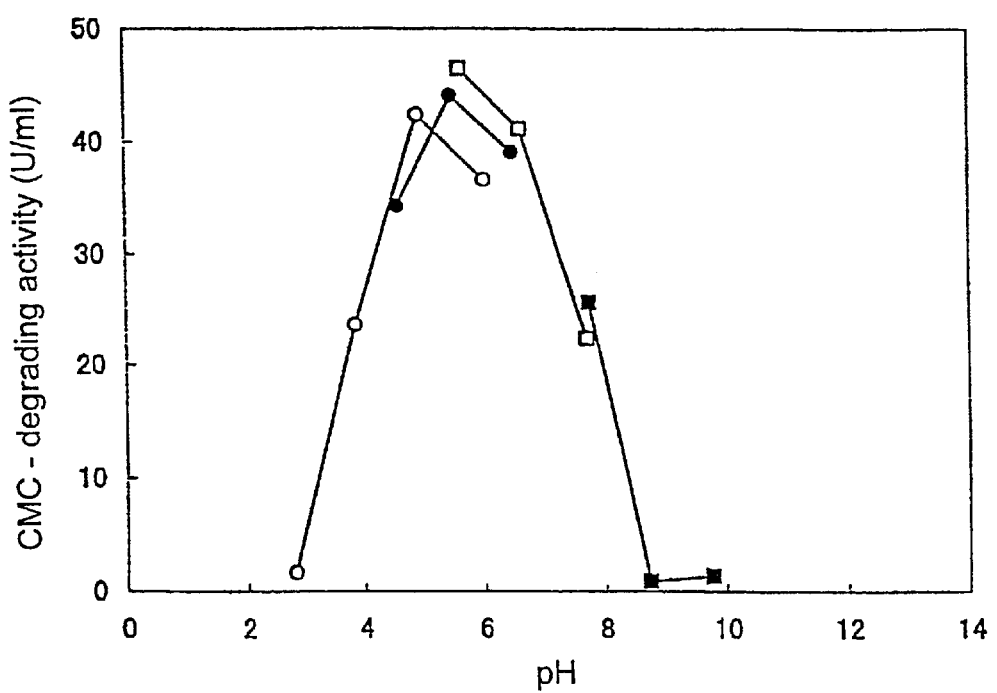
FIG. 4: a figure which illustrates the relationship between the treatment pH and the CMC-degrading activity of the polypeptide of the present invention when the polypeptide was heated at 95° C. for 10 minutes.

The results are shown in FIG. 4. FIG. 4 illustrates the relationship between the pH and the remaining CMC-degrading activity when the polypeptide was heated at 95° C. for 10 minutes. The horizontal axis represents the pH upon heating and the vertical axis represents the remaining CMC-degrading activity (U/ml). Open circles (○), closed circles (●), open squares (□) and closed squares (■) represent the results for sodium citrate buffers, MES-NaOH buffers, Tris-HCl buffers and glycine-NaOH buffers, respectively.

The CMC-degrading activity of the polypeptide of the present invention exhibited the maximal stability at pH 5 to 7.

(5) Heat Stability

CMC was dissolved in 0.1 M MES-NaOH buffer (pH 6.0) to prepare a 1% CMC solution (pH 6.0). 50 μl of the MES buffer was added to 50 μl of the polypeptide solution of the present invention. The mixture was heated at 95° C. for 0, 1, 5 or 24 hours. 50 μl of the 1% CMC solution was added to 50 μl of a 50-, 200- or 500-fold dilution of a supernatant obtained by centrifuging the heated mixture with the MES buffer. The mixture was reacted at 98° C. for 20 minutes. The amount of reducing sugar contained in the reaction mixture was measured according to the Park and Johnson method to determine the CMC-degrading activity.

Figure 5:
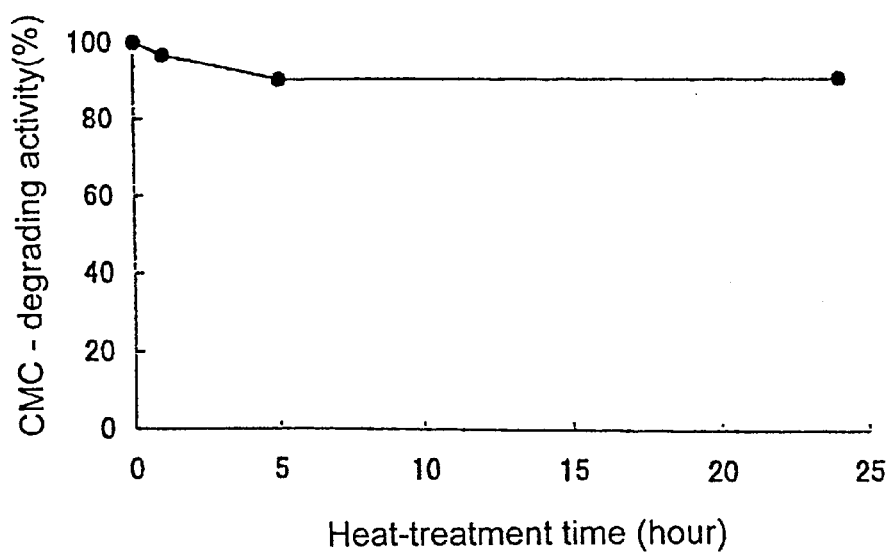
FIG. 5: a figure which illustrates the relationship between the treatment time and the CMC-degrading activity of the polypeptide of the present invention when the polypeptide was heated at 95° C.

The results are shown in FIG. 5. FIG. 5 illustrates the relationship between the heat-treatment time and the remaining activity after heating. The horizontal axis represents the heat-treatment time (hour) and the vertical axis represents the remaining activity (%) after heating.

The polypeptide of the present invention retained about 90% of the CMC-degrading activity after heating at 95° C. for 24 hours.

(6) Degrading Activity on Synthetic Substrate

50 μl of 10 mM pNPC solution in 0.1 M MES-NaOH buffer (pH 6.0) was added to 50 μl of the polypeptide solution of the present invention or a 2-, 5- 10- or 20-fold dilution thereof with 0.1 M MES-NaOH buffer (pH 6.0). The mixture was reacted at 98° C. for 20 minutes. Absorbance at 405 nm of a supernatant obtained by centrifugation was measured to determine the pNPC-degrading activity based on the amount of released p-nitrophenol (pNP).

Figure 6:
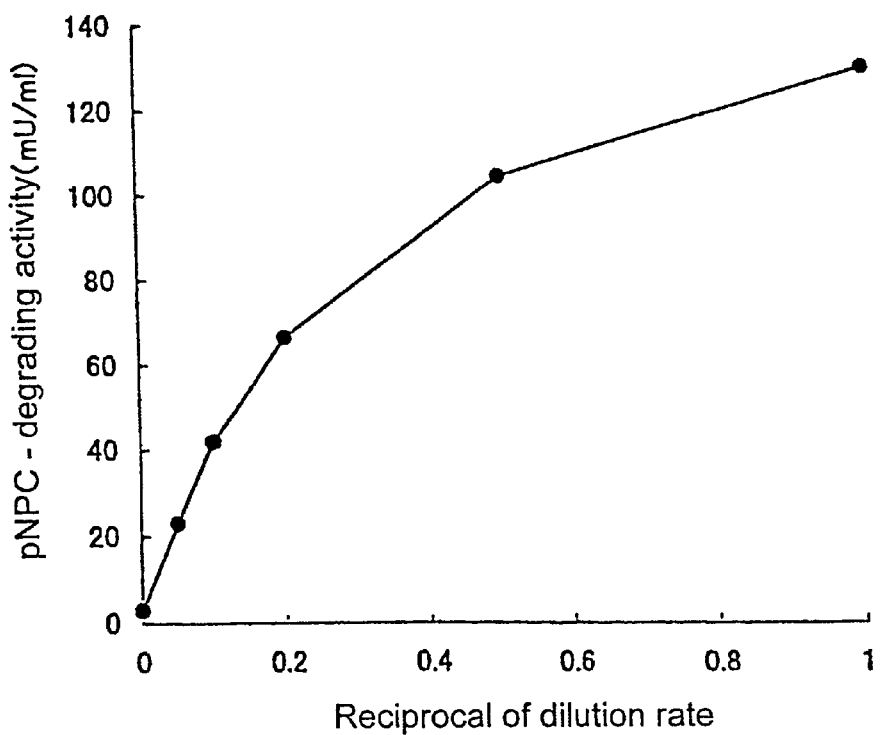
FIG. 6: a figure which illustrate the relationship between the pNPC-degrading activity of the polypeptide of the present invention and the amount of the polypeptide of the present invention.

The results are shown in FIG. 6. FIG. 6 illustrate the relationship between the dilution rate of the polypeptide solution of the present invention and the pNPC-degrading activity of each dilution. The horizontal axis represents the reciprocal of the dilution rate and the vertical axis represents the pNPC-degrading activity (mU/ml).

The pNPC-degrading activity was increased depending on the concentration of the polypeptide solution of the present invention.

(7) Inhibition by Glucose and Cellobiose 50 mM MES-NaOH buffer (pH 6.0) containing 0, 10, 20, 50, 100 or 200 mM glucose or 0, 5, 10, 25 or 50 mM cellobiose, 0.4, 0.8, 1.2 or 1.6 mM pNPC and the polypeptide solution of the present invention was reacted at 98° C. for 20 minutes and absorbance at 405 nm was measured. The reciprocal of the absorbance at 405 nm (vertical axis) was plotted versus the concentration of glucose or cellobiose (horizontal axis). An intersecting point of the lines obtained by linking the points for the respective pNPC concentrations was determined. An inhibition constant Ki was determined by reversing the plus or minus sign of the value of the intersecting point on the horizontal axis.

Since the inhibition of the pNPC-degrading activity of the polypeptide of the present invention by glucose was little, it was impossible to calculate Ki. On the other hand, Ki for cellobiose was 212 mM.

(8) Effects of Various Reagents 50 mM MES-NaOH buffer (pH 6.0) containing 0, 0.5, 1, 2 or 10 mM $CoCl_2$, $CuCl_2$, $CaCl_2$, $FeCl_3$, $ZnCl_2$, $MgCl_2$, dithiothreitol (DTT) or ethylenediaminetetraacetic acid (EDTA), 5 mM p-nitrophenyl-β-D-cellobioside (pNPC, Sigma) and the polypeptide solution of the present invention was reacted at 98° C. for 20 minutes and absorbance at 405 nm was measured. The pNPC-degrading activity was calculated using a calibration curve that represents the relationship between the p-nitrophenol (pNP) concentration and the absorbance at 405 nm. 1 unit (U) of the pNPC-degrading activity of the polypeptide of the present invention is defined as an amount which releases 1 μmol of pNP in 1 minute in the above-mentioned reaction mixture.

Figure 7:
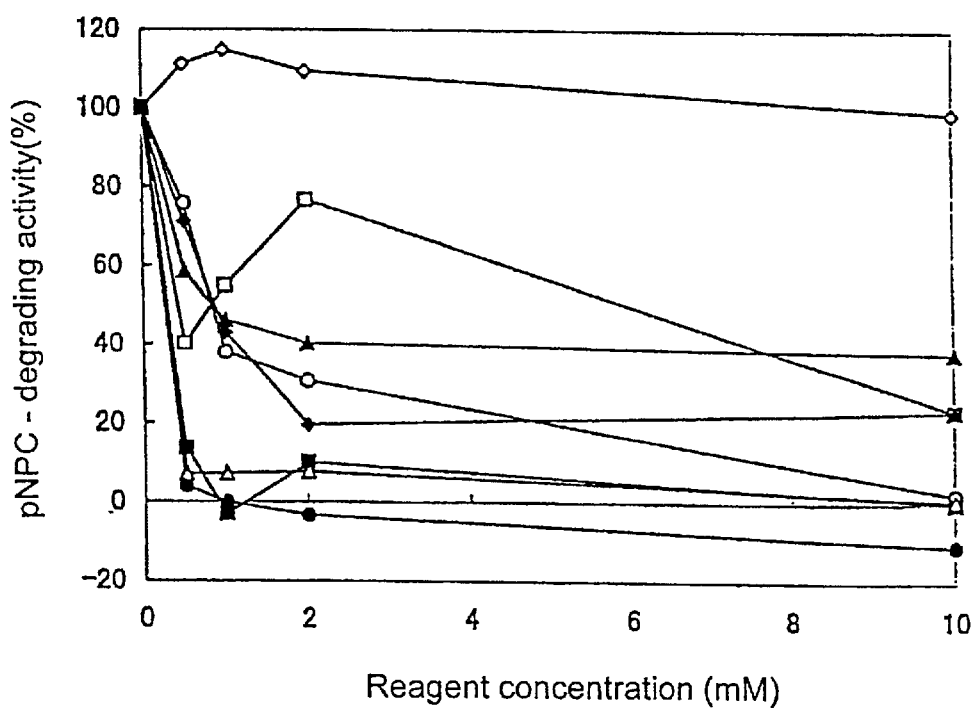
FIG. 7: a figure which illustrates the effects of the various reagents on the pNPC-degrading activity of the polypeptide of the present invention.

The results are shown in FIG. 7. FIG. 7 illustrates the relationship between the various reagents and the pNPC-degrading activity. The horizontal axis represents the concentration of the reagent (mM) and the vertical axis represents the pNPC-degrading activity (relative value, %) In FIG. 7, open circles (○), closed circles (●), open squares (□), closed squares (■), open triangles (Δ), closed triangles (▲), open diamonds (◇) and closed diamonds (◆) represent the results for $CoCl_{21}$ $CuCl_{21}$ $CaCl_2$, $FeCl_{31}$ $ZnCl_{21}$ $MgCl_2$, DTT and EDTA, respectively.

The pNPC-degrading activity of the polypeptide of the present invention was not inhibited by DTT. About 90% of the activity was inhibited by $Cu^{2+}$, $Fe^{3+}$ or $Zn^{2+}$ at a concentration of 0.5 mM. About 50% of the activity was inhibited by $Co^{2+}$, $Ca^{2+}$, $Mg^{2+}$ or EDTA at a concentration of 1 mM.

(9) Purification of the Polypeptide of the Present Invention

An expressed polypeptide solution was prepared as described in Example 2-(2) except that the heat-treatment was at 75° C. for 20 minutes.

A supernatant obtained by centrifuging the heated supernatant was subjected to anion exchange chromatography using HiTrap Q column (Pharmacia). The sample was applied to two 5 ml HiTrap Q columns connected in series. Elution was carried out using a linear gradient in 20 minutes from 50 mM MES-NaOH buffer (pH 6.0) to the same buffer containing 200 mM NaCl at a flow rate of 2 ml/minute. 50 μl of 6 mM 4-MUC solution in 100 mM MES-NaOH buffer (pH 6.0) was added to 50 μl of one of the serial dilutions of the respective fractions. The mixture was reacted at 98° C. for 20 minutes. Fluorescence value was measured at an excitation wavelength of 355 nm and an emission wavelength of 460 nm. The 4-MUC-degrading activity was calculated based on the amount of released 4-MU.

The active fraction from the anion exchange column chromatography was subjected to hydrophobic column chromatography using HiTrap phenyl Sepharose 6 Fast Flow (low sub) (Pharmacia). Saturated ammonium sulfate was added to the active fraction from the anion exchange column chromatography to 20% saturation. The mixture was applied to the hydrophobic column (a volume of 1 ml) equilibrated with 20% saturation ammonium sulfate. Elution was carried out using a linear gradient in 15 minutes from the MES buffer containing ammonium sulfate at 20% saturation to the MES buffer without ammonium sulfate at a flow rate of 1 ml/minute. A 4-MUC-degrading activity was detected in a fraction eluted using about 0% saturation ammonium sulfate.

(10) Determination of Specific Activity 2 ml of the active fraction from the hydrophobic column chromatography was desalted by ultrafiltration, lyophilized and then hydrolyzed in the presence of gas-phase HCl at 135° C. for 3 hours. The hydrolysate was dissolved in 100 μl of water. Analysis of 50 μl of the solution using an amino acid analyzer (L-8500, Hitachi) revealed that the analyzed sample contained 3.61 μg of protein. The polypeptide corresponding to 60 mU of the 4-MUC-degrading activity was subjected to the amino acid analysis. Thus, the specific activity was determined to be 17.0 U/mg. The thus obtained purified polypeptide exhibited physical and chemical properties similar to those determined in Example 3.

(11) Analysis of N-terminal Amino Acid Sequence

The purified polypeptide prepared in Example 3-(9) was subjected to SDS-polyacrylamide gel electrophoresis according to a conventional method. After electrophoresis, the gel was washed in 100 mM succinate buffer (pH 5.8) containing 10 mM DTT and then reacted in 100 mM succinate buffer (pH 5.8) containing 1 mM 4-MUC at 60° C. for 1 hour. A fluorescent band was observed when the gel was irradiated with an ultraviolet ray at 340 nm.

Proteins contained in the gel was transferred to a polyvinylidene difluoride (PVDF) membrane according to a semi-dry blotting method. The membrane was stained with Coomassie Brilliant Blue (CBB). A portion of the PVDF membrane was cut off. This portion corresponded to a band which exhibited a 4-MUC-degrading activity and which was stained with CBB. The N-terminal amino acid sequence was analyzed using a peptide sequencer.

The sequence of six amino acid residues at the N-terminus was Glu-Asn-Thr-Thr-Tyr-Gln (residues 1–6 of SEQ ID NO:1). Accordingly, it was demonstrated that 28 amino acid residues at the N-terminus had been removed from the polypeptide of the present invention expressed in *Escherichia coli*.

EXAMPLE 4

Production of the Polypeptide of the Present Invention Using *Bacillus subtilis*

(1) Construction of Expression Vector for *Bacillus subtilis*

A plasmid pNAPS1 as described in WO 97/21823 was constructed, digested with HindIII (Takara Shuzo) and subjected to agarose gel electrophoresis. A DNA fragment of about 4.5 Kb containing a replication origin for *Bacillus subtilis*, a promoter for subtilisin gene and a sequence encoding secretion signal for subtilisin was extracted and purified from the agarose gel according to a conventional method. pUC119 (Takara Shuzo) was digested with HindIII and dephosphorylated with alkaline phosphatase. These DNA fragments were ligated using DNA ligase. Transformation of *Escherichia coli,* cultivation of transformants as well as extraction and purification of plasmids were carried out according to conventional methods. A plasmid in which the 4.5-kb DNA fragment was inserted such that the lac promoter in pUC119 and the promoter for subtilisin gene were positioned in opposite directions was selected from the thus obtained plasmids and designated as pUC119-BV.

pECEL101 constructed in Example 1 was digested with BamHI and subjected to agarose gel electrophoresis. A DNA fragment of about 1.5 Kb which encodes a portion from leucine residue at position 19 to the termination codon in the open reading frame PH1171 was extracted and purified from the agarose gel according to a conventional method. pUC119-BV obtained as described above was digested with BamHI and subjected to agarose gel electrophoresis. A DNA fragment of about 4.5 Kb containing a replication origin for *Bacillus subtilis* and the like was extracted and purified from the agarose gel according to a conventional method. These DNA fragments were ligated using DNA ligase. Transformation of *Bacillus subtilis* DB104, cultivation of transformants as well as extraction and purification of plasmids were carried out according to conventional methods.

A plasmid in which the open reading frame PH1171 was inserted in the same direction as that of the promoter for subtilisin gene in the vector was selected from the thus obtained plasmids and designated as pNCEL101. The plasmid pNCEL101 encodes a fusion polypeptide downstream from the promoter for subtilisin gene which operates constitutively in *Bacillus subtilis*. In the fusion polypeptide, a leader sequence of 31 amino acid residues derived from the vector including a secretory signal sequence for subtilisin consisting of 29 amino acid residues at the N-terminus is connected with the PH1171 starting from leucine residue at position 19. During the selection of this plasmid, a plasmid in which the open reading frame PH1171 was inserted in the opposite direction to the promoter for subtilisin gene in the vector and a plasmid resulting from self-ligation of the vector were obtained and designated as pNCEL001 and pNBV, respectively. These plasmids were used as vector controls for examining the expression.

(2) Expression of the Polypeptide of the Present Invention

*Bacillus subtilis* DB104 transformed with pNCEL101, pNCEL001 or pNBV obtained as described above was inoculated into LB medium containing 10 μg/ml of kanamycin and cultured aerobically at 37° C. overnight. A CMC-degrading activity in the culture was measured as described in Example 2-(1) using the resulting culture in place of the cell-free extract.

Specifically, 50 μl of one of the cultures of *Bacillus subtilis* transformants and 50 μl of 1% CMC solution in 100 mM sodium citrate buffer (pH 5.0) were mixed together, and the mixture was overlaid with mineral oil. After incubation at 98° C. for 60 minutes, the mixture was centrifuged to recover a supernatant. The reducing power of the reaction mixture was measured according to the Park and Johnson method as described in Example 2-(1). The reaction mixture for which the culture of *Bacillus subtilis* DB104 transformed with pNCEL101 was used exhibited a clearly higher reducing power than that of the reaction mixture for which the culture of DB104 transformed with the plasmid pNBV resulting from self-ligated of the vector was used (control). The CMC-degrading activity, which was calculated based a reducing power determined by subtracting the value for the control and converting to the amount of corresponding glucose, was 0.63 mU/ml culture. For the plasmid pNCEL001 in which PH1171 was inserted in the opposite direction, only a reducing power equivalent to that for pNBV was observed.

EXAMPLE 5

Degradation of Paper Using the Polypeptide of the Present Invention 25 mg of Kimwipe (Crecia) was cut into pieces of about 1 mm square. 480 μl of 50 mM MES-NaOH (pH 6.0) and 20 μl of the same buffer or the cell-free extract from *Escherichia coli* transformed with pECEL211 prepared in Example 2-(1) were added thereto. The mixture was reacted at 95° C. for 66 hours. 100 μl of acetonitrile was added to 50 μl of a supernatant obtained by centrifugation. Insoluble substances were removed by centrifugation. The supernatant was evaporated under reduced pressure to dryness. The residue was re-dissolved in 10 μl of 50% acetonitrile aqueous solution. 1 μl of the solution was subjected to silica gel thin-layer chromatography as described in Example 2-(2).

As a result, a spot with the same Rf value as that for cellobiose was observed only for the sample to which the cell-free extract from *Escherichia coli* transformed with pECEL211 was added.

INDUSTRIAL APPLICABILITY

The present invention provides a polypeptide having a cellobiohydrolase activity. The polypeptide of the present invention has high heat resistance and is capable of efficiently degrade cellulose. Since glucose can be efficiently produced from cellulose by using the polypeptide of the present invention in combination with endoglucanase, exo-1,4-β-D-glucosidase and β-D-glucosidase derived from extreme thermophiles, utilization of cellulose-type biomass is facilitated.

Sequence Listing Free Text

SEQ ID NO:3: Designed oligonucleotide primer designated as 1171FN to amplify a 1.6-kb DNA fragment containing the open reading frame PH1171.

SEQ ID NO:4: Designed oligonucleotide primer designated as 1171RA to amplify a 1.6-kb DNA fragment containing the open reading frame PH1171.

What is claimed is:

1. A nucleic acid encoding a polypeptide having a cellobiohydrolase activity, which is selected from the group consisting of:
   (1) a nucleic acid encoding the polypeptide having the amino acid sequence of SEQ ID NO:1;
   (2) a nucleic acid which has the nucleotide sequence of SEQ ID NO:2; and
   (3) a nucleic acid which is capable of hybridizing to the nucleotide sequence of SEQ ID NO:2 under stringent conditions and which encodes the polypeptide having a cellobiohydrolase activity.

2. A polypeptide which is encoded by the nucleic acid to claim 1.

3. The polypeptide according to claim 2, wherein said polypeptide has a cellobiohydrolase activity and has an inhibition constant Ki of 10 mM or more for cellobiose.

4. The polypeptide according to claim 2, wherein said polypeptide retains 20% or more of the cellobiohydrolase activity after treatment of 95° C. for 5 hours.

5. A method for degrading a polymer of D-glucopyranose bonded through β-1,4 bonds, comprising allowing the polypeptide according to claim 2 to act on a polymer of D-glucopyranose bonded through β-1,4 bonds to release cellobiose.

6. A recombinant DNA containing the nucleic acid according to claim 1.

7. A host cell transformed with the recombinant DNA according to claim 6.

8. A method for producing the polypeptide having cellobiohydrolase activity, comprising:
   culturing the transformed host cell of claim 7; and
   collecting a polypeptide having cellobiohydrolase activity from the culture.

* * * * *